United States Patent [19]
Bier

[11] Patent Number: 6,096,310
[45] Date of Patent: Aug. 1, 2000

[54] ORAL IMMUNOTHERAPY OF BACTERIAL OVERGROWTH

[76] Inventor: Milan Bier, 4730 E. Placita Elegante, Tucson, Ariz. 85718

[21] Appl. No.: 08/839,618

[22] Filed: Apr. 15, 1997

[51] Int. Cl.$^7$ .......................... A61K 39/395; A61K 39/40; A61K 39/42; A61K 39/44
[52] U.S. Cl. ...................... 424/130.1; 424/167.1; 424/246.1; 424/278.1; 424/178.1; 424/163.1; 424/157.1; 424/164.1; 530/388.1; 530/387.1
[58] Field of Search ............... 424/167.1, 130.1, 424/246.1, 278.1, 178.1, 163.1; 530/388.1, 387.1

[56] References Cited

U.S. PATENT DOCUMENTS

| | | | |
|---|---|---|---|
| Re. 33,565 | 4/1991 | Stolle et al. | 424/87 |
| 4,477,432 | 10/1984 | Hardie | 424/85 |
| 4,486,282 | 12/1984 | Bier . | |
| 5,017,372 | 5/1991 | Hastings . | |
| 5,233,997 | 8/1993 | Klein et al. . | |
| 5,443,826 | 8/1995 | Broody . | |
| 5,506,213 | 4/1996 | Carson et al. . | |
| 5,698,195 | 12/1997 | Le et al. . | |
| 5,725,861 | 3/1998 | Teichmann et al. . | |
| 5,744,134 | 4/1998 | Paul . | |

OTHER PUBLICATIONS

Tacket et al, New Eng. J. Med. 318: 1240–1243, 1988.
Soudah et al, New. Eng. J. Med. 325: 1461–1467, 1991.
Sjogren, Arthritis & Rheumatism, 37/9: 1265–1282, 1994.
May et al. Scand. J. Gastroenterol, 19: 916–922, 1994.
Lock et al, Am.J. Gastroenterol, 92/5: 763–771, 1997.
Job et al, Drug Safety 17/1: 37–46, 1997.
Sjogren, Current Opin. Rheumatol 8:569–575, 1996.
Reinauer et al. Acta. Derm. Venerol. 74: 361–63, 1994.
Owyang Gut, 1994, Suppl 3: 511–514.
Verne et al. Digestive Diseases & Sciences, 1995, 40/9: 1892–901.
Young et al. Rheum. Dis. Clin. North.Am. 1996, 22/4: 797–823
Rose et al, Gastroenterol. Clin. North.Am. 1998, 27/3: 563–94.
Folwaczny et al, 1996, Z. Gastroenterol. 34/8: 497–508.
AuBuchon et al, Annals of Internal Medicine, 1997, 127/10:904–909.
Toskes, New Eng. J. Medicine, 1991 325/2: 1508–1509.

*Primary Examiner*—Nita Minnifield
*Attorney, Agent, or Firm*—Kenyon & Kenyon

[57] ABSTRACT

The object of the present invention is the oral administration of animal immunoglobulins for the treatment of gastrointestinal disorders caused by bacterial and/or yeast overgrowth. Immunoglobulins derived from the blood, plasma or serum of animals, such as cow, goats, sheep and pigs, contain a broad spectrum of antibodies to bacteria and yeast that afflict the gastrointestinal tract of human patients.

16 Claims, No Drawings

ORAL IMMUNOTHERAPY OF BACTERIAL OVERGROWTH

FIELD OF THE INVENTION

The present invention relates to a method for treatment of gastrointestinal bacterial overgrowth using orally administered immunoglobulins derived from animal blood, plasma or serum.

BACKGROUND OF RELATED ART

Bacterial overgrowth is a condition in which the normal gastrointestinal bacterial flora is overtaken by proliferation of undesirable bacteria. It frequently occurs in patients in a weakened state of health, such as patients with compromised immunity, including transplant patients, AIDS patients, scleroderma patients, etc. The condition is usually marked by bloating, diarrhea and/or constipation, liquid stools, uncontrollable belching, and/or esophagal refluxing. S. A. Kaye et al., British Journal of Rheumatology, Vol. 34, p. 265 (1995) describes the condition of small bowel bacterial overgrowth in systemic sclerosis.

In some cases the overgrowth is due to a specific bacterium, such as a *C. difficile*, in other cases it may be due to a mixture of bacterial species and other organisms such as yeast, parasitic pathogens or viral pathogens.

Known treatments for gastrointestinal bacterial overgrowth include a variety of antibiotics, sulfa drugs and anti-yeast medications. Unfortunately, these medications, while often effective, are only useful for limited time periods since prolonged administration can cause serious complications such as selective propagation of antibiotic-resistant populations often more noxious, such as *C. difficile*. Antibiotics, sulfa drugs and anti-yeast medications do not eliminate the underlying cause of the bacterial overgrowth, and thus, gastrointestinal bacterial overgrowth is likely to recur in an aggravated form upon cessation of treatment. Furthermore, other undesirable consequences occur when the administration of antibiotics, sulfa drugs and anti-yeast medications is terminated, such as, for example, new overgrowth with different pathogens.

It is well known that immunoglobulins are the first line of defense against pathogens, and it is generally recognized that the main activity of immunoglobulins is in the circulating blood. A notable exception is the colostrum, the first postpartum milk, rich in immunoglobulins of the IgG and IgA type. These immunoglobulins protect newborn mammals which have immature immune systems against infections. This passive immunization via colostrum has been recognized for a long time as being particularly important for neonate survival.

Use of colostrum or its derivatives for the treatment of some gastroenteric diseases has been reported. See, for example, C. O. Tacket et al., Enterotoxigenic *Escherichia coli* (frequent cause of traveller's diarrhea), The New England Journal of Medicine, Vol. 318, p. 1240, 1988; P. Heaton, Case Report: Persistent Diarrhea, Archives of Diseases in Childhood, Vol. 65, p. 813, 1990; and Traveller diarrhea, Lancet, Editorial, p. 144, 1988.

Immunoglobulins, mainly immunoglobulin G, abbreviated "IgG", can be isolated from human plasma by a variety of techniques, well known in the art. Use of isolated immunoglobulins for intramuscular use or more highly purified immunoglobulins for intravenous usage is known in the medical arts. U.S. Pat. No. 4,477,432 discloses the oral administration of human immunoglobulins to prevent or treat enteric infections in humans.

Prior to the present invention described herein, it was generally assumed that only human immunoglobulins, i.e., immunoglobulins derived from human blood, plasma or serum, could be used for the treatment of human diseases. Furthermore, it is known that an intramuscular or intravenous use of immunoglobulins derived from animals such as goats, cows and horses is likely to cause a variety of undesirable side effects, such as serious allergic reactions, serum sickness, or anaphylactic shock.

SUMMARY OF THE INVENTION

It is an object of the present invention to provide safe and effective use of preparations of immunoglobulins derived from animals, i.e., non-human immunoglobulins, such as, for example, goats, cows, horses, sheep, and pigs for the oral treatment of bacterial overgrowth in humans.

For example, unless specifically allergic to bovine meat, a very rare occurrence, oral administration of bovine immunoglobulins is well tolerated by humans because the ingested immunoglobulins in a normal adult are not adsorbed into the blood stream and thus, their activity is restricted to their immediate environment, i.e., the human digestive system, where their antibacterial and/or antiviral activity is desired. After the ingested immunoglobulins have provided their desired activity, the immunoglobulins are eventually digested by the proteolytic enzymes of the stomach and gut. Prior to digestion by the proteolytic enzymes, the immunoglobulins of the present invention have a sufficient half-life in the system to substantially inhibit or reduce bacterial overgrowth.

In accordance with the present invention, the survival time of the animal derived immunoglobulins in the human gastrointestinal tract can also be improved by various strategies commonly used in medicine to modify the pH of the stomach, such as administration of antacids or acid release inhibitors. These reduce the acidity of the stomach, where pepsin is the main digestive enzyme. Pepsin is optimally active in acid media, thus modification of the pH of the stomach results in a reduction in pepsin activity.

Alternatively, for those patients not suffering from bacterial overgrowth in the stomach, but rather suffering from bacterial overgrowth in other portions of the gastrointestinal tract, the immunoglobulins of the present invention can be administered as a dry powder, enterically coated to entirely bypass the stomach.

The advantage of using animal derived immunoglobulins, in particularly cow, sheep, goat, pig or horse immunoglobulins, over human immunoglobulins are numerous. Animal immunoglobulins are more readily accessible and are less costly. Moreover, the animal product is also far safer, for human donors are potential carriers of very serious disease vectors, including hepatitis and HIV. Even the best screening of human donor blood from which the immunoglobulins are isolated, cannot guarantee absence of these vectors. To the contrary, animals, such as cows, horses, pigs, sheep and goats, do not carry any of these viral human disease vectors. It can also be fairly assumed that these animals have been exposed over their lifetime to the same range of potential pathogens as human patients and have therefore built up the requisite reservoir of antibodies. For patients suffering from chronic disease, it may be necessary to continue the immunoglobulin treatment for a long period of time, even possibly for the life of the patient, therefore, safety and cost of the immunoglobulin treatment are of paramount importance.

The use of blood, plasma or serum derived animal immunoglobulins is preferred over those derived from milk or colostrum because plasma is readily obtainable at all times. Thus, hyperimmunization of the donor animal, if needed, can be carried out routinely at any time. In contrast, colostrum is only obtainable from female mammals in limited quantities only during immediate postpartum. Further, milk, as distinct from colostrum, carries very low concentrations of immunoglobulins and is not usually considered a practical source of immunoglobulins.

In accordance with the present invention, a donor animal may be hyperimmunized to produce immunoglobulins against any specific infectious agent, such as a *C. difficile*. Alternatively, immunoglobulins derived from the natural spectrum of animal antibodies, such as bovine or equine immunoglobulins can be administered to the human patient.

DETAILED DESCRIPTION

Animal derived immunoglobulins suitable for use with the present invention are IgA, IgD, IgE, IgG and IgM. IgG is the most preferred immunoglobulin for treating bacterial overgrowth in accordance with the present invention. Preferably, at least 50% of the immunoglobulins administered in accordance with the present invention are IgG immunoglobulins. The blood, plasma or serum animal derived immunoglobulins herein are orally administered in doses preferably between about 100 mg and about 1,800 mg per day.

Immunoglobulins derived from animal plasma are readily available in commerce and have previously been used for non-therapeutic purposes such as immunochemical tests. Immunoglobulins derived from animal plasma suitable for use in accordance with the present invention are commercially available from CalBiochem-Novabiochem International of San Diego, Calif., ICN Biomedicals, Inc. of Costa Mesa, Calif., and Sigma Chemical Co. of St. Louis, Mo.

A number of methods for the isolation of immunoglobulins from blood, plasma or serum are well known in the art. They include the methods of ethanol fractionation, chromatography, electrophoresis, and precipitation with zinc ions.

The method of isolation of immunoglobulins from blood, plasma or serum by precipitation with zinc ions is preferred because of its ease of use. Isolation of immunoglobulins by precipitation with zinc ions was first described in detail by Cohn, E. J., (J. L. K. Tullis ed.) *Blood Cells and Plasma Proteins*, Academic Press, New York (1953). A method of precipitation with zinc ions is also described in U.S. Pat. No. 4,486,282 to Bier which is incorporated herein by reference. Zinc ions are non-toxic and may have numerous beneficial effects. See C. F. Mills, Editor: *Zinc in Human Biology*, Springer-Verlag, 1989.

Such methods for the isolation of immunoglobulins result in protein preparations containing a preponderance of immunoglobulins of type IgG. Methods for isolating immunoglobulins which provide at least 50% IgG are preferred.

In accordance with the present invention the therapeutic immunoglobulins can be administered to the patient in a variety of ways. The simplest, as exemplified in Example 1, is as a suspension of the protein in a small amount of water or buffered water. Alternatively, the protein can be administered as a dry powder including additives as deemed desirable to assure rapid dissolution when ingested. Suitable additives for use with the immunoglobulins of the present invention are, for example, mannose, sorbitol, lactose, colloidal silicon, polyethylene glycol and microcrystalline cellulose. The protein can also be administered as a zinc complex, or can be enterocoated for delayed dissolution so that it bypasses the stomach.

Of particular importance in choosing the proper formulation is the prolongation of the protein antibacterial activity upon ingestion. The use of antacids has been mentioned above. Alternatively, the protein may be administered bound to or adsorbed on a solid support medium, as commonly utilized in affinity chromatography. The choice of the medium and methods of attachment are well known in the art. An alternative medium for achieving prolongation of the immunoglobulin antibacterial activity is the administration of natural vegetable mucilloid fiber, commonly utilized for "regularity" of the digestive track, for example, METAMUCIL®, in combination with the animal derived immunoglobulins of the present invention.

If desired, the animal derived immunoglobulins described herein can be administered in combination with an antiyeast drug to control gastrointestinal yeast overgrowth. Suitable antiyeast drugs for administration in combination with the immunoglobulins of the present invention are nystatin, diflucan, mycostatin and mycelex.

EXAMPLE 1

The subject, a 68 year old woman suffering from scleroderma for about three years, had severe reflux, bloating, hiccups, frequent liquid diarrhea while still constipated, being unable to fully empty the bloated digestive system. Bacterial overgrowth of the subject's digestive system was confirmed by gastric endoscopy and ascribed to the reduced motility of the esophagus and bowels, as a result of scleroderma.

The subject's symptoms were not alleviated by restricted diet, which avoided mainly food with indigestible components, such as present in vegetables, fruits, whole wheat bread, etc. Nor did her condition improve through conventional therapeutic treatment, which included daily dosage with PROPULSID®, an oral gastrointestinal agent available from Janssen Pharmaceutica, PRILOSEC®, a gastric acid inhibitor available from Astra pharmaceuticals daily injections of OCTREOTIDE®, an inhibitor of the release of vasoactive intestinal peptide and other factors, available from Novartis and several bouts of treatment with sulfa drugs and antibiotics, including erythromycin. None of these alleviated the patients symptoms, to the contrary her reaction to SULFATRIM® suspension, a sulfa drug, was particularly severe, resulting in serum sickness, symptomatically revealed as an acute bout of arthritic joint swelling and pain. Because of the reflux, the patient slept in a semi-inclined position, adjusted by an electric bed. As a result of her condition, the subject's weight decreased from about 130 lbs to 104 lbs in a few months.

In an attempt to treat the bacterial overgrowth, the subject was put on a regime of oral blood derived bovine immunoglobulins. The protein was purchased in 25 gm lots from CalBiochem-Novabiochem International of San Diego, Calif. (Cat. #345876; Bovine gamma globulin, serum), as a white freeze-dried powder. Variable dose of between 100 and 600 mg of protein were dissolved in roughly 15 ml tap water, and swallowed first thing in the morning and last thing at night. Later on, the regime was modified to include also a mid-day dose. The protein solution is slightly turbid, but otherwise tasteless and odorless.

To further validate the treatment, during the last two months of treatment, bovine immunoglobulins obtained from Sigma Chemical Co. of St. Louis, Mo. (Cat. No. G 5009; Bovine gamma globulin, from Cohn fraction 2) were orally administered to the patient three times a day at a variable dose of between 100 and 600 mg of protein dissolved in roughly 15 ml tap water.

The effect of the treatment was striking. Within a few days of the treatment, both reflux and bloating vanished nearly completely. The patient was able to switch to a much broader, nearly normal diet, which was well tolerated. Her liquid diarrhea ceased, replaced by normal formed stool. These beneficial effects continued for over six months and the patient remains in far better condition than at any time in the previous 2 years. During this period there was one minor relapse, as an after-effect of 7 days dosage with an antibiotic administered for treatment of severe bronchitis. This relapse cleared within three days of cessation of antibiotic administration through continued administration of the immunoglobulins. For the last two months of the treatment, the patient was also administered nystatin, an antifungal medication, in addition to the immunoglobulins. Administration of this medication prior to the protein therapy had no obvious beneficial effect, but was added at that time to ensure even better control of the overgrowth and it seemed to be well tolerated.

To further validate the treatment, subsequent to the treatment described above, the patient was treated with a different preparation of bovine immunoglobulins obtained from Sigma Chemical Co. of St. Louis, Mo. (Cat. No. G 5009; Bovine gamma globulin, from Cohn fraction 2). This preparation also provided effective control of the patient's gastrointestinal bacterial overgrowth.

I claim:

1. A method for treatment of bacterial overgrowth associated with scleroderma comprising oral administration of non-human immunoglobulins derived from circulatory fluids selected from the group consisting of blood, plasma and serum.

2. The method according to claim 1, wherein the fluids are obtained from animals selected from the group consisting of cows, horses, goats, sheep and pigs.

3. The method according to claim 1, wherein the immunoglobulins contain at least about 50% IgG.

4. The method according to claim 3, wherein the immunoglobulins are administered orally in doses between about 100 mg and about 1,800 mg per day.

5. The method according to claim 1, wherein the immunoglobulins comprise an aqueous suspension.

6. The method according to claim 1, wherein the immunoglobulins comprise an enterocoated dry powder for preventing dissolution of the immunoglobulins in acid media.

7. The method according to claim 1, wherein the immunoglobulins are derived from animals hyperimmunized to specific antigens comprising at least one human gastric pathogen.

8. The method according to claim 1, further comprising administration of an antacid in combination with the immunoglobulins.

9. The method according to claim 1, wherein the immunoglobulins are administered in combination with an anti-yeast drug.

10. The method according to claim 9, wherein the anti-yeast drug is selected from the group consisting of nystatin, diflucan, mycostatin and mycelex.

11. The method according to claim 1, wherein the immunoglobulins are administered as a zinc-protein complex.

12. The method according to claim 1, further comprising administering the immunoglobulins in combination with natural vegetable mucilloid fiber.

13. The method according to claim 1, wherein the bacterial overgrowth is associated with systemic schleroderma.

14. The method according to claim 3, wherein the fluids are of bovine origin.

15. The method according to claim 3, wherein the bacterial overgrowth is associated with systemic scleroderma.

16. The method according to claim 14, wherein the fluids are bovine plasma.

* * * * *